United States Patent [19]

Dillon et al.

[11] Patent Number: 4,675,409

[45] Date of Patent: Jun. 23, 1987

[54] PROCESS FOR THE PREPARATION OF ENCAINIDE

[75] Inventors: John L. Dillon, Clay; Richard H. Spector, Fayetteville, both of N.Y.

[73] Assignee: Bristol-Myers Company, New York, N.Y.

[21] Appl. No.: 833,295

[22] Filed: Feb. 25, 1986

[51] Int. Cl.⁴ .................. C07D 211/34; C07D 211/02
[52] U.S. Cl. ...................................... 546/185; 546/234
[58] Field of Search ................................ 546/234, 185

[56] References Cited

U.S. PATENT DOCUMENTS

| | | |
|---|---|---|
| 3,931,195 | 1/1976 | Dykstra et al. |
| 4,000,143 | 12/1976 | Dykstra et al. |
| 4,064,254 | 12/1977 | Dykstra et al. |
| 4,394,507 | 7/1983 | Madding ............................ 546/185 |

OTHER PUBLICATIONS

Dykstra et al, *J. Med. Chem.*, vol. 16, No. 9, pp. 1015–1020 (1973).
Byrne, et al., *J. Pharmacology and Experimental Therapeutics,* vol. 200, No. 1, pp. 147–154 (1977).
Horwitz, *Journal of Organic Chemistry,* vol. 21, pp. 1039–1041 (1956).
Stanek, et al., *Chem. Abstracts,* 49, 314h (1955).
Phillips, *Journal of Organic Chemistry,* vol. 12, pp. 333–341 (1947).

*Primary Examiner*—Norma S. Milestone
*Attorney, Agent, or Firm*—Richard P. Ryan; Robert E. Carnahan

[57] ABSTRACT

A new and novel process for the preparation of encainide (4-methoxy-2'-[2-(1-methyl-2-piperidyl)ethyl]-benzanilide) has been developed. The process utilizes α-picoline, O-nitrobenzaldehyde, and anisoyl chloride as starting materials.

3 Claims, No Drawings

PROCESS FOR THE PREPARATION OF ENCAINIDE

BACKGROUND OF THE INVENTION

This invention embodies a new and novel process for the preparation of encainide (I)

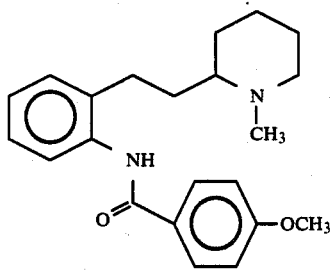

Encainide, chemically, 4-methoxy- 2'-[2-(1-methyl-2-piperidyl) ethyl ]benzanilide, is a member of a series of antiarrhythmic 2-phenethylpiperidines bearing amide substituents in the ortho-position of the phenyl ring. Encainide hydrochloride is also referred to in the literature as MJ 9067-1 (USAN and the USP Dictionary of Drug Names, 1980, p. 122, United States Pharmacopeal Convention, Inc., 12601 Twinbrook Parkway, Rockville, MD. 20852, Library of Congress Catalog Card No. 72-88571). Currently, encainide is undergoing clinical evaluation as an effective antiarrhythmic agent.

Previous syntheses of encainide and closely related compounds are described in the following references.

Dykstra, S. J., et al., J. Med. Chem., 16, 1015-1020, (1973).

S. J. Dykstra and J. L. Minielli, U.S. Pat. No. 3,931,195 patented Jan. 6, 1967; U.S. Pat. No. 4,000,143 patented Dec. 28, 1978; U.S. Pat. No. 4,064,254 patented Dec. 20, 1977.

Byrne, J. E., et al., J. Pharmacology and Experimental Therapeutics, 200, 147-154 (1977).

Another process, different from syntheses disclosed in the above-cited references, is described in U.S. Pat. No. 4,394,507, which issued July 19, 1983.

The instant process differs from these previously disclosed processes and offers advantages that will be evident from the description of the invention.

The following references relate to condensation of aromatic aldehydes with quaternized α-picolinium halides.
  a. Horwitz, Journal of Organic Chemistry, 21, 1039-1041 (1956).
  b. Stanek, et al., Chem. Abstracts, 49, 314h (1955).
  c. Phillips, Journal of Organic Chemistry, 12, 333-341 (1947).

The condensation process disclosed and discussed in the above references a–c does not proceed readily with o-nitrobenzaldehyde, affording yields of only 40% or less of condensation product.

There is nothing in any of the above references or any other prior art that would suggest or make obvious the novel process embodied in the present invention. Summary of the Invention This invention relates to a new process for the preparation of encainide which has the formula

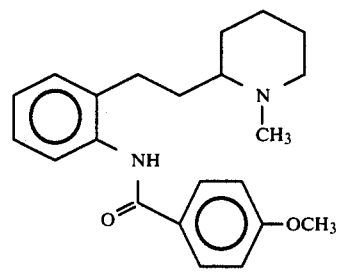

or the hydrochloride acid addition salt thereof starting with α-picoline, o-nitrobenzaldehyde, and anisoyl chloride. Detailed Description of the Invention The following flow chart, Scheme 1, illustrates the preparation of encainide from readily available starting materials utilizing the instant process.

Scheme 1

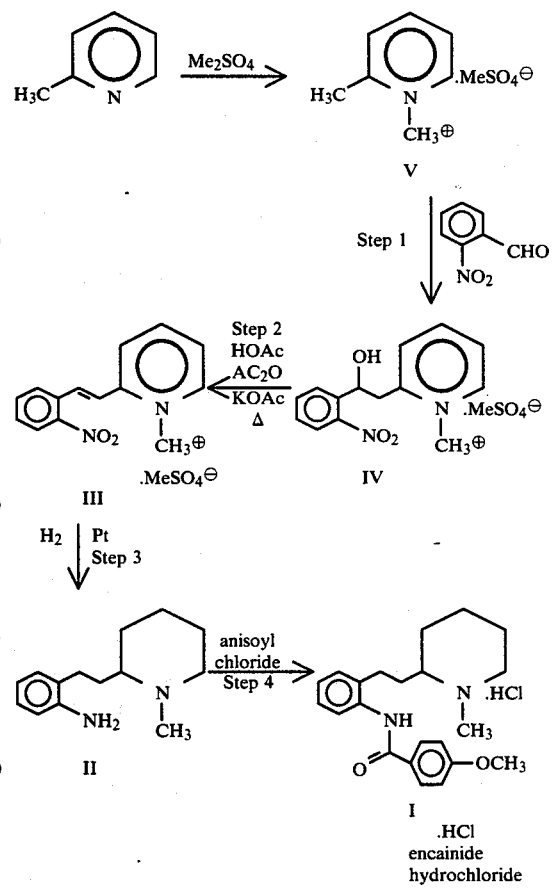

This invention relates to a new and novel synthesis of encainide. It was an object of the present invention to develop a method of synthesis for encainide having a minimal number of steps and which would start with o-nitrobenzaldehyde which is now available commercially as a bulk chemical commodity. Another object of the invention was to design a process which was more economical in terms of consumption of expensive noble metal catalysts, e.g. prior art processes require two hydrogenation steps and/or use of both platinum and palladium. Finally, it was an object of the present invention to produce a final product in the form of a pure white solid, lacking the varying degrees of pink color which characterized product produced by prior art methods.

The objectives of the present invention have been achieved by the process which will be described in detail below.

The first step of the process outlined in Scheme 1 involves the condensation of o-nitrobenzaldehyde with the picolinium methyl sulfate salt (V; generated in situ from dimethylsulfate and α-picoline). The quaternizing use of dimethylsulfate instead of the commonly employed methyl halides facilitates the aldehyde +α-picoline condensation and leads to very high yields of the alcohol product IV. Simple mixing of the reactants in an inert organic solvent, such as methylene chloride, results in high yield (92-94) of the alcohol product IV which can be conveniently isolated by filtration. This facile, high yield condensation, achieved in two hours at room temperature as opposed to prior art conditions of 50 hours in refluxing acetic anhydride, when α-picoline and o- nilrobenzaldehyde are condensed appears to be due to the use of dimethylsulfate as the quaternizing agent.

In order to capitalize on this significant improvement in product yield from the condensation reaction, it was necessary to overcome poor results in the dehydration step of IV to III. Attempts to dehydrate IV to III (step 2) in a manner analogous to that of the quaternary halide salts, specifically the bromide, met with significant complications and low yield. It was subsequently discovered that the addition of a catalytic amount of potassium acetate to the dehydrating mixture of acetic acid and acetic anhydride resulted in production of the olefin III in greater than 90% yield. This olefin product III, as envisioned, is now suitably disposed for the simultaneous reduction of all three functional moieties (nitro, olefin, pyridinium) to form the requisite functional moieties (amino, alkylene, piperidine) of the encainide molecule. These reductions are simultaneously accomplished in step 3 by catalytic hydrogenation using platinum metal catalyst to give the diamine intermediate II. The hydrogenation process is accomplished using an alcoholic solution of III, 95% ethanol being preferred. The diamine product II is isolated as an oil following neutralization and extraction with an immiscible solvent such as methylene chloride. As an added advantage, the Pt catalyst recovered from this step does not suffer significant poisoning, as in prior art processes, but may be recycled.

The final reaction (step 4) leads to the desired final product, encainide hydrochloride, in form of a white solid lacking the contaminating pink coloration often appearing in product produced by other processes. It was discovered that this conversion of II to encainide hydrochloride of high purity could be accomplished by simply adding anisoyl chloride to a solution of the diamine intermediate II in an appropriate organic solvent such as acetone, acetonitrile, or an alcohol. An appropriate solvent is one in which compound II and p-anisoyl chloride are soluble but encainide HCl is not. The most preferred solvent for this step is acetone. In the use of alcohols, $C_{2-5}$ alkanols such as propanol, butanol, and so forth are intended. This facile acylation reaction also proceeds very cleanly with a surprising lack of any significant amounts of hydrochloride salt products of II appearing. Liberated HCl is effectively scavenged by the base form of newly formed 1. If required, encainide free base of high purity may be obtained in the usual manner from the encainide hydrochloride produced in the subject process. Recrystallized encainide hydrochloride is obtained in 55-60% yield from compound III in the new process.

In summary, the process of the instant invention meets the objectives set forth hereinabove. It is a new four-step process which uses o-nitrobenzaldehyde as a starting material, achieves economic savings with the single catalyst hydrogenation step employed, and provides pure product lacking the color impurities which frequently occurred in prior art processes.

DESCRIPTION OF SPECIFIC EMBODIMENTS

The process of this invention is illustrated in greater detail by the following examples directed to preferred embodiments of the hereinabove described process steps. These examples, however, should not be construed as limiting the scope of the present invention in any way.

EXAMPLE 1

1-(2-Nitrophenyl)-2-[2-(1-methyl)-pyridinium Methyl Sulfate]-ethanol (IV)

Dimethylsulfate (59.0 mL, 78.5 g, 0.62 moles) was added in one portion to a solution of -picoline (65.3 mL, 61.6 g, 0.66 moles) in 650 mL dry methylene chloride being stirred under a nitrogen atmosphere. A gentle reflux of the methylene chloride solvent resulted and the reaction mixture was stirred for 18 hours. The o-nitrobenzaldehyde (95 g, 0.63 moles) was added and after solution was achieved, a small amount of piperidine (3.9 mL) was also added. The solid product formed over the next two hours and, following cooling to 5°, it was isolated by filtration. The filtrate was washed with a 350 mL portion of methylene chloride and dried in vacuo at 25° for 6 hours to yield from 214-219 g (92-94%) of IV as an off-white crystalline solid. Analytically pure material, m.p. 157.5°-159.5°, was obtained by recrystallization from isopropanol-methanol.

Anal. Calcd. for $C_{15}H_{18}N_2O_7S$ (MW =370.39): C, 48.64; H, 4.91; N, 7.56. Found: C, 48.71; H, 4.91, N, 7.38.

EXAMPLE 2

2-(2-Nitrostyrenyl)-1-methyl-pyridinium Methyl Sulfate (III)

A reaction mixture of 1-(2-nitrophenyl)-2-[2-(1-methyl) pyridinium methyl sulfate]-ethanol (IV; 100 g, 0.27 moles), glacial acetic acid (400 mL), acetic anhydride (150 mL), and potassium acetate (2 g) was refluxed for 2 hours. (The reaction is amenable to being monitored by means of TLC: silica, 10% acetic acid in methanol.) The reaction solution was cooled to approximately 40°and the solvents removed in vacuo. Isopropyl alcohol (600 mL) was added to the residual yellow oil and this resulted in formation of a pale yellow solid. This yellow mixture was stirred, cooled to 5°, filtered, and the salt was washed with an additional 250 mL of isopropyl alcohol and dried in vacuo at 25°for 6 hours to give 86-92 g (90-97%) of product III as a pale yellow crystalline solid. Analytically pure material, m.p. 145°-146°was obtained by recrystallization from isopropanol-methanol.

Anal. Calcd. for $C_{15}H_{16}N_2O_6S$: C, 51.12; H, 4.59; N, 7.95. Found: C, 50.82; H, 4.60; N, 7.90.

EXAMPLE 3

2-(2-Aminophenethyl)-1-methylpiperidine (II)

2-(2-Nitrostyrenyl)-1-methylpyridinium methyl sulfate (III; 25 g, 0.07 moles) and 10 g of 5% Pt on carbon (50% water wet) in 300 mL of 95% ethanol was put in a 2L Parr hydrogenation flask and hydrogenated at approximately 2 psi of hydrogen for 16 hours. The hydrogenation mixture rapidly turned orange and then slowly became colorless as the organic solid dissolved. Catalyst was removed by filtration and held for subsequent runs. The filtrate was concentrated in vacuo to an oil which was dissolved in 50 mL water and made basic (pH~11) with 50% sodium hydroxide solution. The basic aqueous phase was extracted with 50 and 25 mL portions of methylene chloride, the extracts were combined and dried (anhyd. $K_2CO_3$), filtered and the solid removed in vacuo to yield 14.3 g (92%) of product II as an amber oil. This intermediate diamine oil (cf: U.S. 3,931,195; Example 1) was used directly in the next step of the process.

EXAMPLE 4

Encainide Hydrochloride 4—Methoxy—2'—8 2—(1—methyl—2—piperidy)—ethyl]benzanilide Hydrochloride; I—HCl)

Unpurified 2-(2-aminophenethyl)-1-methylpiperidine (II; 14.3 g, 0.066 moles) was dissolved in 100 mL dry acetone and p-anisoyl chloride (12.1 g, 0.071 mole) was added. The reaction mixture was stirred for 16 hours, cooled to 5o, and filtered. The solid material was washed with 25 mL of cold acetone and dried in vacuo at 25o for 6 hours. The dried solid was recrystallized from isopropanol-methanol to give 15.5 g of encainide hydrochloride, m.p. 183°–185°.

Anal. Calcd. for $C_{22}H_{29}ClN_2O_2$, C, 67.93; H, 7.53; N, 7.20. Found: C, 68.06; H, 7.60; N, 7.12. This represents an overall yield from compound III of 56%.

What is claimed is:

1. A process for preparing 4-methoxy-2'-[2-(1-methyl-2-piperidyl) ethyl]benzanilide (I) as the hydrochloride salt

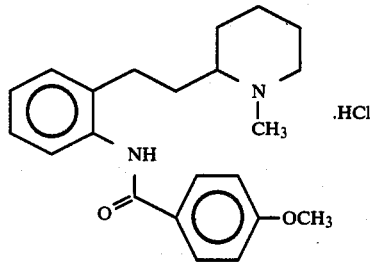

I (HCl)

which comprises
   (a) combining α-picoline and dimethylsulfate to form the picolinium methyl sulfate salt (V)

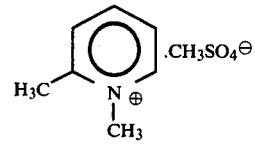

V which is then reacted with o-nitrobenzaldehyde to produce 1-(2-nitrophenyl)-2-[2-1-methyl) pyridinium methyl sulfate]-ethanol (IV)

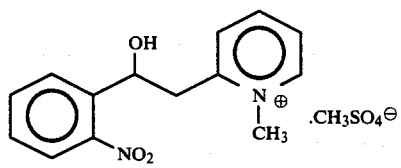

IV (b) dehydrating (IV) by heating in a mixture of acetic acid, acetic anhydride and potassium acetate to yield 2-(2-nitrostyrenyl)-[2-(1-methyl) pyridinium methyl sulfate ] (III);

III (c) hydrogenating (III) using a platinum catalyst to generate 2-(2-aminophenethyl)-1-methylpiperidine (II); and

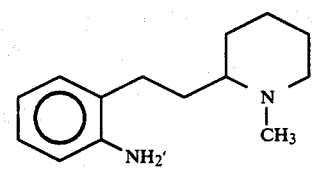

II (d) reacting (II) with anisoyl chloride in an organic solvent selected from the group consisting of acetone, acetonitrile, and a $C_{2-5}$ alkanol, to obtain encainide hydrochloride directly.

2. The process of claim 1 wherein the platinum catalyst is 5% Pt on carbon.

3. The process of claim 1 wherein the reaction of (II) with anisoyl chloride is carried out in acetone media.

* * * * *